United States Patent
Yim et al.

(10) Patent No.: US 9,539,227 B2
(45) Date of Patent: *Jan. 10, 2017

(54) PHARMACEUTICAL COMPOSITION FOR THE PREVENTION OR TREATMENT OF INFLAMMATORY DISEASES OR IMMUNE DISEASES CONTAINING RAMALIN

(71) Applicant: Korea Ocean Research and Development Institute, Incheon (KR)

(72) Inventors: Joung Han Yim, Gyeonggi-do (KR); Il Chan Kim, Gyeonggi-do (KR); Sung Gu Lee, Incheon (KR); Doc Kyu Kim, Incheon (KR); Se Jong Han, Gyunggi-do (KR); Hyoung Seok Lee, Seoul (KR); Sung Jin Kim, Incheon (KR); Tai Kyoung Kim, Incheon (KR); Pil-Sung Kang, Incheon (KR); Heeyong Park, Gyeonggi-do (KR); Ha Ju Park, Gyeonggi-do (KR); Suhkneung Pyo, Seoul (KR); Babita Paudel-Bhattarai, Goettingen (DE)

(73) Assignee: KOREA OCEAN RESEARCH AND DEVELOPMENT INSTITUTE, Incheon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/261,551

(22) Filed: Apr. 25, 2014

(65) Prior Publication Data

US 2014/0235719 A1 Aug. 21, 2014

Related U.S. Application Data

(63) Continuation of application No. 13/701,113, filed as application No. PCT/KR2011/004049 on Jun. 2, 2011, now abandoned, application No. 14/261,551, filed on Apr. 25, 2014, which is a continuation-in-part of application No. 13/128,586, filed as application No. PCT/KR2009/006562 on Nov. 10, 2009, now Pat. No. 8,809,578.

(30) Foreign Application Priority Data

Nov. 10, 2008 (KR) .................. 10-2008-0111021
Jun. 3, 2010 (KR) .................. 10-2010-0052551

(51) Int. Cl.
*A61K 31/198* (2006.01)
*A61K 45/06* (2006.01)
*A61K 31/45* (2006.01)

(52) U.S. Cl.
CPC ............ *A61K 31/198* (2013.01); *A61K 31/45* (2013.01); *A61K 45/06* (2013.01)

(58) Field of Classification Search
CPC ............ A61K 31/198; A61K 2800/522; A23V 2200/02; C07C 243/34

See application file for complete search history.

(56) References Cited

U.S. PATENT DOCUMENTS

| | | | |
|---|---|---|---|
| 5,789,395 A | 8/1998 | Amin et al. | |
| 6,489,308 B1 | 12/2002 | Shapiro | |
| 2006/0105989 A1* | 5/2006 | Takagaki ................. | A23L 1/30 514/54 |
| 2010/0086627 A1 | 4/2010 | Zabrecky | |
| 2013/0116324 A1 | 5/2013 | Yim et al. | |
| 2013/0211133 A1 | 8/2013 | Yim et al. | |

FOREIGN PATENT DOCUMENTS

| | | |
|---|---|---|
| JP | 2005-82531 A | 3/2005 |
| KR | 1998-0008216 A | 4/1998 |
| KR | 10-2010-0052130 A | 5/2010 |
| WO | 2010053327 A2 | 5/2010 |

OTHER PUBLICATIONS

Hilbig, V.S.; Andries, T.; Steglich, W.; Anke, T. "Zur Chemie und antibiotischen Aktivitat des Carbolegerlings (Agaricus xanthoderma" Angew. Chemie. 1985, 97 (12) 1063-1064.*
Translation of Hilbig reference.*
Hasler, C.M. "Functional Foods: Benefits, Concerns and Challenges—A Position Paper from the American Council on Science and Health" J. Nutr. Dec. 1, 2002, 132, 12, 3772-378.*
Spann, C.T.; Taylor, S.C.; Weinberg, J.M. "Topical Antimicrobial Agents in Dermatology" Clinics in Dermatology 2003, 21, 70-77.*
DermNetNZ (http://www.dermnetnz.org/dermatitis/atopic-causes.html) Sep. 30, 2015, pp. 1-4.*

(Continued)

*Primary Examiner* — Brian-Yong Kwon
*Assistant Examiner* — Andrew S Rosenthal
(74) *Attorney, Agent, or Firm* — Hultquist, PLLC; Mary B. Grant (57) ABSTRACT

The present invention relates to the novel use (anti-inflammatory activity) of Ramalin isolated from the Antarctic lichen *Ramalina terebrata*, and more specifically to a pharmaceutical composition containing Ramalin as an active ingredient. Ramalin of the invention is a compound derived from natural material, has no toxicity or side effects, and inhibits the expression of inducible nitric oxide synthase (iNOS) in the transcription stage to significantly inhibit the production of nitric oxide (NO) that is a key mediator of inflammatory responses. In addition, it inhibits the activation of the inflammatory mediator NF-κB, inhibits p38 MAPK, ERK1/2 and JNK signaling pathways, and inhibits the expression of the LPS receptor TLR4, suggesting that Ramalin has an excellent anti-inflammatory effect. Thus, the composition containing Ramalin can be effectively used to fundamentally treat or prevent inflammatory diseases or immune diseases and to relieve or alleviate the symptoms of the diseases.

15 Claims, 5 Drawing Sheets

(56) References Cited

OTHER PUBLICATIONS

Ahmed, A.U. "An overview of inflammation: mechanism and consequences" Front. Biol. 2011, 6(4): 274-281.*

Baber, N. et al. "Indomethacin in rheumatoid arthritis: clinical effects, pharmacokinetics, and platelet studies in responders and nonresponders" 1979, Annals of the Rheumatic Diseases, 38, 128-137.*

Zumla, A. et al. "Tuberculosis" 2013, N Engl J Med 368, 8, pp. 745-755, supplemental pp. 1-13.*

Thaiwat, S.; Sangasapaviliya, A. "Omalizumab treatment in severe adult atopic dermatitis" Asian Pac J Allergy Immunol 2011; 29:357-60.*

Paudel-Bhattarai, B. PhD dissertation titled: "Isolation and Characterization of Antibacterial and Antioxidant Compounds from the Antarctic Lichen *Ramalina terebrata*" Dept of Biology, Graduate School of Soonchunhyang University. Jan. 2009.*

Bhattarai, H.D. et al. "Thin layer chromatography analysis of antioxidant constituents of lichens from Antarctica" J Nat Med (2008) 62:481-484.*

Paudel, B. et al. "Antibacterial Potential of Antarctic Lichens against Human Pathogenic Gram-positive Bacteria" Phytother. Res. 22, 1269-1271 (2008).*

Ahmadjian, V., "The Lichen Symbiosis", Jun. 1993, pp. 17, Publisher: John Wiley & Sons, Inc., Published in: New York.

Babu, B., et al., "Design of isoform-selective inhibitors of nitric oxide synthase", "Current Opinion in Chemical Biology", Aug. 1998, pp. 491-500, vol. 2.

Behera, B., et al., "Determination of antioxidative potential of lichen *Usnea ghattensis* in vitro", "Lebensm. Wiss. Technol. (LWT)", Jan. 2006, pp. 80-85, vol. 39.

Bhattarai, H., et al., "Thin layer chromatography analysis of antioxidant constituents of lichens from Antarctica", "J Nat Med", Jun. 17, 2008, pp. 481-484, vol. 62.

Blake, G., et al., "Tumour necrosis factor-alpha, inflammatory biomarkers, and atherogenesis", "European Heart Journal", Oct. 2, 2001, pp. 345-347, vol. 23.

Brocklehurst, W., "Role of Kinins and Prostaglandins in Inflammation", "Proc. Roy. Soc. Med.", Jan. 1971, pp. 4-6, vol. 64.

Butler, A., "The biological roles of nitric oxide", "Chemistry and Industry", Oct. 16, 1995, pp. 828-830, vol. 20.

Gallo, R., et al., "Biology and clinical relevance of naturally occurring antimicrobial peptides", "J Allergy Clin Immunol", Dec. 2002, pp. 823-831, vol. 110.

Hasler, C., "Functional Foods: Benefits, Concerns and Challenges—A Position Paper from the American Council on Science and Health", "J. Nutr.", Dec. 1, 2002, pp. 3772-3781, vol. 132, No. 12.

Hawiger, J., "Innate Immunity and Inflammation: A Transcriptional Paradigm", "Immunologic Research", Apr.-Jun. 2001, pp. 99-109, vol. 23, No. 2/3.

Hilbig, V., et al., "Zur Chemie und antibiotischen Aktivitaet des Carbolegerlings (Agaricus xanthoderma)", "Angew. Chem.", Dec. 1985, pp. 1063-1064, vol. 97, No. 12.

Huang, A., et al., "Effects of Systemic Inflammation on Endothelium-Dependent Vasodilation", "Trends Cardiovasc. Med.", Jan. 2006, pp. 15-20, vol. 16, No. 1.

Kerwin, Jr., J., et al., "Nitric Oxide: A New Paradigm for Second Messengers", "Journal of Medicinal Chemistry", Oct. 27, 1995, pp. 4343-4362, vol. 38, No. 22.

Mueller, K., "Pharmaceutically relevant metabolites from lichens", "Appl Microbiol Biotechnol", May 29, 2001, pp. 9-16, vol. 56.

Paudel, B., et al., "Antibacterial activities of Ramalin, usnic acid and its three derivatives isolated from the Antarctic lichen *Ramalina terebrata*", "Z. Naturfosch C.", Jan.-Feb. 2010, pp. 34-38, vol. 65, No. 1/2.

Paudel, B., et al., "Antibacterial activities of Ramalin, usnic acid and its three derivatives isolated from the Antarctic lichen Ramalina terebrata", "Z. Naturrosch C.", Jan.-Feb. 2010, pp. 34-38 (Abstract), vol. 65, No. 1/2, PubMed Citation—accessed May 9, 2013.

Paudel-Bhattarai, B., B. PhD dissertation titled: "Isolation and Characterization of Antibacterial and Antioxidant Compounds from the Antarctic Lichen *Ramalina terebrata*", Jan. 2009, Publisher: Department of Biology, Graduate School of Soonchunhyang University.

Renauld, J-C., "New insights into the role of cytokines in asthma", "J Clin Pathol", Aug. 2001, pp. 577-589, vol. 54.

Ryan, G., et al., "Acute inflammation. A review.", "Am J. Pathol", Jan. 1977, pp. 183-276, vol. 86, No. 1.

Spann, C., et al., "Dis. Mon.", Jul. 2004, pp. 407-421, vol. 50, No. 7.

Yamaki, K., et al., "Characteristics of histamine-induced leukocyte rolling in the undisturbed microcirculation of the rat mesentery", "British Journal of Pharmacology", Feb. 1998, pp. 390-399, vol. 123, No. 3.

Park, H., et al., "Ramahne Inhibits LPS-induced NO Release in Macrophages by Regulating MAPK and NF-kappa B Activities", "FASEB", Apr. 30, 2010, vol. 24.

Sharma, J., et al., "Role of Nitric Oxide in Inflammatory Diseases", "Inflammopharmacology", Dec. 12, 2006, pp. 252-259, vol. 54.

* cited by examiner

PHARMACEUTICAL COMPOSITION FOR THE PREVENTION OR TREATMENT OF INFLAMMATORY DISEASES OR IMMUNE DISEASES CONTAINING RAMALIN

CROSS-REFERENCE TO RELATED APPLICATIONS

This application is a continuation under the provisions of 35 U.S.C. §120 of U.S. patent application Ser. No. 13/701,113 filed Nov. 30, 2012, which is a U.S. national phase application under the provisions of 35 U.S.C. §371 of International Patent Application No. PCT/KR11/04049 filed Jun. 2, 2011, which in turn claims priority of Korean Patent Application No. 10-2010-0052551 filed Jun. 3, 2010, and this application is also a continuation in part under the provisions of 35 U.S.C. §120 of U.S. patent application Ser. No. 13/128,586 filed May 10, 2011, issued as U.S. Pat. No. 8,809,578, which is a U.S. national phase application under the provisions of 35 U.S.C. §371 of International Patent Application No. PCT/KR09/06562 filed Nov. 10, 2009, which in turn claims priority of Korean Patent Application No. 10-2008-0111021 filed Nov. 10, 2008. The disclosures of such U.S. and international patent applications and Korean priority patent applications are hereby incorporated herein by reference in their respective entireties, for all purposes.

TECHNICAL FIELD

The present invention relates to the novel use of Ramalin for treatment of inflammatory disease or immune disease. More specifically, the present invention relates to a pharmaceutical composition for preventing and treating inflammatory disease or immune disease, which contains Ramalin having anti-inflammatory activity or a salt thereof, and a method of preventing or treating inflammatory disease or immune disease using the composition.

BACKGROUND ART

Inflammatory responses are defensive responses which are caused by various factors such as infection with pathogens or injury of tissue in the body and perform initial protective action to limit damage to infected or injured areas. In most cases, such inflammatory responses lead to the removal of pathogenic factors and the induction of adaptive immunity by the components of innate immunity (Hawiger J., Innate Immunity and Inflammation: A Transcriptional Paradigm. Immunologic Research. 23, pp. 99-109, 2001). Rubors, tumors, calors, dolors and the like, known to be accompanied by inflammation, are the results of continuous inflammatory responses, such as an increase in local blood flow and a decrease in local blood flow rate, which result from vasodilation caused by the action of inflammatory mediators and cytokines in the area of inflammation, an increase in the release of plasma components from blood vessels, which results from an increase in the permeability of blood vessels, an increase in the release of immune cells from blood vessels, which results from the adhesion of blood vessel endothelial cells to circulating immune cells, and an increase in migration to an infected area by chemotaxis (Gallo R L, Murakami M, Takaaki O, Zaiou M., Biology and clinical relevance of naturally occurring antimicrobial peptides. J. Allergy. Clin. Immunol. 110, pp. 823-831. 2002; Graeme B. Ryan, M B, and Guido M., Acute Inflammation. American Journal of Pathology. 86(1), pp. 185-274, 1977).

In addition, inflammation-related vasodilation and an increase in the permeability of blood vessels are also attributable to histamines which are produced in some cells in response to tissue injury, and low-molecular-weight peptide kinins which are present in an inactivated state in blood and activated by tissue injury (Yamaki K, Thorlacius H, Xie X, Lindbom L, Hedqvist P, Raud J., Characteristics of histamineinduced leukocyte rolling in the undisturbed microcirculation of the rat mesentry. British J. Pharmacol. 123, pp. 390-399, 1998; Brocklehurst W E, Role of Kinins and Prostaglandins in Inflammation. Proc. Roy. Soc. Med. 64, pp. 4-6, 1971).

Generally, an acute inflammatory response occurs rapidly, is maintained for a short time and is accompanied by a systemic response known as the acute-phase response. Meanwhile, chronic inflammation can result continuous immune activation in connection with some diseases such as infection or autoimmune diseases, and the accumulation and activation of macrophages is the hallmark of chronic inflammation (Huang A L, Vita J A, Effects of Systemic Inflammation on Endothelium-Dependent Vasodilation. Trends, Cardiovasc. Med. 16, p. 1520, 2006). However, continuous chronic inflammatory responses can cause serious damage to host cells or tissue.

Inflammatory responses at the site of infection are initiated by the response of macrophages to pathogens. It is known that reactive oxygen species and reactive nitrogen species (e.g., NO), which are produced by macrophages activated by pathogens, inflammatory mediators such as prostaglandins and leukotrienes, and pro-inflammatory cytokines such as TNF-α, IL-6 and IL-8, are involved in inflammatory responses (Renauld J C, New insights into the role of cytokines in asthma. J. Clin. Pathol. 54, pp. 577-589, 2001; Blake G J, Ridker P M, Tumour necrosis factor-α, inflammatory biomarkers, and atherogenesis. Eur. Heart J. 23, pp. 345347, 2002). The activation of NF-κB that is a transcriptional factor of genes related to the production of inflammatory mediators is very important in the inflammation-related action of macrophages. It was reported that inflammation-related genes, including inducible nitric oxide synthase (iNOS2), cyclooxygenase (COX-2), TNF-α, IL-6, IL-8 and the like, are transcribed by NF-κB in macrophages.

Nitric oxide (NO) is produced from L-arginine by nitric oxide synthase (hereinafter referred to as NOS) in the macrophages of the human body (Kerwin, J. F. et al., J. Med. Chem., 38:4343, 1995). The NOS of the human body has three NOS isomers, including endothelial constitutive NOS (hereinafter referred to as ecNOS), neuronal constitutive NOS (hereinafter referred to as ncNOS) and inducible NOS (hereinafter referred to as iNOS). Among them, ecNOS and ncNOS are expressed in endothelial cells and neuronal cells, respectively, and dependent on calcium and calmodulin, whereas iNOS is highly expressed in various cells only when the cells are activated by lipopolysaccharide (hereinafter referred to as LPS) present in the cell membrane of pathogenic bacteria, cytokines such as IL-1 and TNF-α, and immune stimulants such as radiation, and iNOS is not dependent on calcium and calmodulin. NO functions as a defense against tumor cells and pathogenic bacteria at high concentration, and a low concentration of NO produced in blood vessel endothelial cells functions to regulate blood pressure, and NO produced in neuronal cells performs various physiological responses related to neurotransmitter function, learning, memory and the like. Constitutive NOS (cNOS) plays an important role in maintaining the homeostasis of the human body, and NO produced by ecNOS acts in the blood vessel system to inhibit vasodilation and platelet adhesion or aggregation, and NO produced by ncNOS acts in the nerve system to increase long-term memory or acts as a neurotransmitter to cause melancholia and is involved in the mobility of the digestive tract or the erection of the penis.

On the other hand, NO produced by iNOS expression induced by specific cytokines or LPS is involved in inflammatory expression or host defense mechanisms. The transcriptional factor NF-κB is activated in macrophages by the stimulation of endotoxin to induce iNOS expression, thereby increasing the production of NO (Butler, A. R., *Chemistry & Industry*, 16:828, 1995). It is known that when the expression of iNOS is induced by external stimulation of LPS, inflammation inducers radiation or the like, a large amount of NO is produced continuously for 4-6 hours to cause inflammatory responses in the human body. In the case of rats, large amounts of iNOS mRNA and protein are expressed in macrophages by external stimulation, and NO synthesized by the expression performs antimicrobial action and antitumor action. However, it is known that when NO is produced in excessively large amounts, it causes inflammatory responses, such as arthritis and septicemia, tissue graft rejection, immune diseases such as autoimmune diseases and diabetes, and the death of neuronal cells.

Thus, iNOS activity inhibitors have high potential as agents for treating such diseases, and from this viewpoint, compounds that inhibit NO production caused by iNOS can be used as agents for treating various inflammatory diseases in the human body. Studies on materials that inhibit the production of NO have been conducted mainly on the development of materials that specifically inhibit the enzymatic activity of iNOS. Specifically, studies have been conducted on the development of derivatives of the precursor L-arginine, derivatives of L-citrulline, derivatives of amino guanidine, derivatives of isothiourea, etc., (Babu, B. R. B. and Griffith O. W., *Current Opinion in Chemical Biology*, 2:491, 1998).

However, the regulation of expression of iNOS in the transcription stage in inflammatory responses is very important in determining the production of NO, and thus there is a need for the development of drugs related to the regulation of NF-κB activity by phosphorylation of IkB which is an inhibitor of the transcriptional factor NF-κB in macrophages, or drugs related to Akt, ERK, c-jun- and p38-MAPK signaling pathways which are related to the regulation of NF-κB activity.

Lichens are similar to non-flowering plants and are the symbiotic association of fungi (mycobionts) with algae and/or cyanobacteria (photobionts). The fungi in lichens form thalli or lichen substrates containing typical secondary metabolites (Ahmadjin V., *The lichen symbiosis*, Wiley, New York, pp. 1-6, 1993). It is difficult to obtain sufficient amounts of natural lichen samples, and technology of cultivating large amounts of lichens is not known. For this reason, studies on lichens were relatively insufficient compared to studies on higher plants. As the tissue culture method, mass-production method and biological analysis method for lichens have been improved, studies thereon have been actively conducted (Behera, B. C. et al., *Lebensm. Wiss. Technol.*, 39:805, 2006). Compounds having various biological activities (including cytotoxicity, antifungal, antimicrobial, antioxidant and anti-inflammatory activities), including fatty acids, depsides, depsidones, dibenzofurans, diterpenes, anthraquinones, naphtoquinones, usninic acid, pulvinic acids, xanthones and epidithiopiperazinediones, were isolated from lichens (Muller, K., Appl. *Microbiol. Biotechnol.*, 56:9-16, 2001).

*Ramalina terebrata* is a lichen that grows naturally in the Antarctic King George Island and can be easily collected from the King George Island. During studies on the Antarctic lichen *Ramalina terebrata*, the present inventors previously isolated the novel compound Ramalin having excellent antioxidant activity (Korean Patent Application No. 2008-111021). However, there has been no report that Ramalin has anti-inflammatory activity.

Accordingly, the present inventors have examined the cellular immunity inhibitory activity of Ramalin by conducting comparative experiments in vitro and in vivo in order to determine the effect of Ramalin on the LPS-induced production of NO in mouse macrophage RAW264.7 cells, and as a result, have found that Ramalin has the effect of inhibiting inflammatory responses. More specifically, the present inventors have found that Ramalin of the present invention inhibited the mRNA expression of iNOS to significantly inhibit the production of NO, inhibited the activation of NF-κB, inhibited p38 MAPK, ERK1/2 and JNK signaling pathways, inhibited the expression of the LPS receptor TLR4, and showed excellent anti-inflammatory and immune regulatory effects in in vivo experiments, thereby completing the present invention.

DISCLOSURE OF INVENTION

Technical Problem

It is an object of the present invention to provide the novel use of Ramalin having anti-inflammatory and immune regulatory activities.

Technical Solution

To achieve the above object, the present invention provides a pharmaceutical composition for preventing or treating inflammatory disease or immune disease, which contains, as an active ingredient, Ramalin having a structure of the following formula 1 or a pharmaceutically acceptable salt thereof:

[Formula 1]

In the present invention, Ramalin functions to inhibit the expression of iNOS gene to inhibit the excessive production of nitric oxide (NO).

In the present invention, the inflammatory disease or immune disease may be atopic dermatitis, arthritis, urethritis, cystitis, arteriosclerosis, allergic disease, nasitis, asthma, acute pain, chronic pain, paradentitis, gingivitis, inflammatory bowel disease, gout, myocardial infarction, congestive heart failure, hypertension, angina pectoris, stomach ulcer, cerebral infarction, Down's syndrome, multiple sclerosis, obesity, diabetes, dementia, depression, schizophrenia, tuberculosis, sleep disorder, sepsis, a burn, pancreatitis, Parkinson's disease, stroke, brain damage caused by seizure, or autoimmune disease.

In the present invention, the composition may further contain a suitable carrier, excipient or diluent which is corn only used in preparation of pharmaceutical compositions.

In the present invention, the composition may be formulated or used in combination with one or more agents selected from the group consisting of anti-histamine agents, anti-inflammatory agents, anticancer agents and antibiotics.

The present invention also provides the use of Ramalin having a structure of formula 1 or a pharmaceutically acceptable salt thereof for preventing or treating inflammatory disease or immune disease.

The present invention also provides a method of preventing or treating inflammatory disease or immune disease using Ramalin having a structure of formula 1 or a pharmaceutically acceptable salt thereof.

The present invention also provides a method for preventing or treating inflammatory disease or immune disease, the method comprising a step of treating (administrating) a subject with Ramalin having a structure of formula 1 or a pharmaceutically acceptable salt thereof.

The present invention also provides a functional food and functional cosmetic product for preventing or improving inflammatory disease or immune disease, which contain, as an active ingredient, Ramalin having a structure of formula 1.

BEST MODE FOR CARRYING OUT THE INVENTION

In one aspect, the present invention is directed to the novel use of a compound Ramalin having a structure of the following formula 1:

[Formula 1]

Ramalin of the present invention is a compound isolated from the Antarctic lichen *Ramalina terebrata* and having antioxidant activity. The high-resolution ESI-MS of the Ramalin indicated that the Ramalin has a molecular weight of 254.1141 and is a compound having a molecular formula of $C_{11}H_{16}N_3O_4$ as shown in formula 1. The name "Ramalin" was given because it is a compound isolated from *Ramalina terebrata*.

In the present invention, the anti-inflammatory activity (novel activity) of Ramalin was analyzed, and as a result, it was found that Ramalin inhibits the expression of inducible nitric oxide synthase (iNOS) in the transcriptional stage to significantly inhibit the production of nitric oxide (NO), a key mediator of inflammatory responses, inhibits the phosphorylation of the inflammatory mediator NF-κB, inhibits p38 MAPK, ERK1/2 and JNK signaling pathways, and also inhibits the expression of the LPS receptor TLR4. The results of the analysis will be described in detail in examples below.

The present invention provides the use of Ramalin having a structure of formula 1 or a pharmaceutically acceptable salt thereof for preventing or treating inflammatory disease or immune disease.

The present invention is directed to a pharmaceutical composition for preventing or treating inflammatory disease or immune disease, which contains, as an active ingredient, Ramalin having a structure of formula 1 or a pharmaceutically acceptable salt thereof. In addition, the present invention provides a method of preventing or treating inflammatory disease or immune disease using Ramalin having a structure of formula 1 or a pharmaceutically acceptable salt thereof. In one embodiment, the present invention is directed to a method for preventing or treating inflammatory disease or immune disease, the method comprising a step of treating (administrating) a subject with Ramalin having a structure of formula 1 or a pharmaceutically acceptable salt thereof. Herein, the treatment or administration may be performed in vivo or in vitro.

In the present invention, the inflammatory disease or immune disease may be atopic dermatitis, arthritis, urethritis, cystitis, arteriosclerosis, allergic disease, nasitis, asthma, acute pain, chronic pain, paradentitis, gingivitis, inflammatory bowel disease, gout, myocardial infarction, congestive heart failure, hypertension, angina pectoris, stomach ulcer, cerebral infarction, Down's syndrome, multiple sclerosis, obesity, diabetes, dementia, depression, schizophrenia, tuberculosis, sleep disorder, sepsis, a burn, pancreatitis, Parkinson's disease, stroke, brain damage caused by seizure, or autoimmune disease.

As used herein, the term "inflammatory disease" refers to a disease caused by an inflammatory response induced by an external or internal material, and examples of inflammatory disease include neuroinflammatory diseases and arthritis. As used herein, the term "immune disease" refers to a disease caused by the excessive response of the immune system in the human body, and typical examples of immune disease include allergic diseases. However, because inflammatory disease is ultimately caused by the response of the immune system in the body, the term "inflammatory disease" and the term "immune disease" can be similar to each other in a broad sense, and thus are used interchangeably in the specification.

The pharmaceutical composition according to the present invention can be administered by various routes, including, but not limited to, oral, intravenous, intramuscular, intra-arterial, intramedullary, intradural, intracardial, transdermal, subcutaneous, intraperitoneal, intranasal, gastrointestinal, local, sublingual and rectal routes. Preferably, the composition of the present invention is administered orally or parenterally. As used herein, the term "partenteral" includes subcutaneous, intradermal, intravenous, intramuscular, intraperitoneal, intra-articular, intra-synovial, intrasternal, intrathecal, intralesional and intracranial injection or infusion techniques. The pharmaceutical composition of the present invention may also be administered in the form of suppositories for rectal administration.

The pharmaceutical composition of the present invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The dose level of the pharmaceutical composition of the present invention will depend upon a variety of factors, including the activity of the specific compound employed, the age, body weight, general health status, sex, diet, time of administration, route of administration, rate of excretion, drug combination, and the severity of the specific disease to be prevented or treated. The pharmaceutical composition according to the present invention can be formulated in the form of pills, sugar-coated tablets, capsules, liquid, gel, syrup, slurry or suspensions.

In the present invention, the pharmaceutical composition may be formulated or used in combination with one or more drugs selected from the group consisting of anti-histamine agents, anti-inflammatory agents, anticancer agents and antibiotics.

In another aspect, the present invention is directed to a method for preventing or treating inflammatory disease or immune disease, the method comprising administering a pharmaceutical composition for preventing or treating inflammatory disease or immune disease, which contains, as an active ingredient, Ramalin having a structure of formula 1 or a pharmaceutically acceptable salt thereof.

The inventive pharmaceutical composition and preventing or treating method can be effectively used because they use Ramalin that is a natural material-derived compound having excellent anti-inflammatory activity and having no toxicity and side effects.

In still another aspect, the present invention is directed to a functional food for preventing or improving inflammatory disease or immune disease, which contain, as an active ingredient, Ramalin having a structure of formula 1.

The functional food of the present invention can be used in various applications, including drugs, foods and beverages. Examples of the functional food of the present invention include various foods, candies, chocolates, beverages, gums, teas, vitamin complexes, health supplement foods, and the like, and it can be used in the form of powders, granules, tablets, capsules or beverages. The immune disease or inflammatory disease in the present invention may be atopic dermatitis, arthritis, urethritis, cystitis, arteriosclerosis, allergic disease, nasitis, asthma, acute pain, chronic pain, paradentitis, gingivitis, inflammatory bowel disease, gout, myocardial infarction, congestive heart failure, hypertension, angina pectoris, stomach ulcer, cerebral infarction, Down's syndrome, multiple sclerosis, obesity, diabetes, dementia, depression, schizophrenia, tuberculosis, sleep disorder, sepsis, a burn, pancreatitis, Parkinson's disease, stroke, brain damage caused by seizure, or autoimmune disease.

As evident from the results of analysis of biological mechanisms as described below, Ramalin which contained as an active ingredient in the functional food of the present invention has excellent anti-inflammatory activity. Thus, it will be obvious to those skilled in the art that Ramalin will exhibit excellent effects when it is used in foods.

In yet another aspect, the present invention is directed to a functional cosmetic product for preventing or treating inflammatory disease or immune disease, which contain, as an active ingredient, Ramalin having a structure of formula 1.

The functional cosmetic product of the present invention may be formulated as conventional emulsions and solubilized formulations. The emulsion-type cosmetic formulations include milk lotion, cream, essence and the like, and the solubilized cosmetic formulations include skin lotion.

Examples of cosmetic formulations suitable for the present invention include solutions, gels, anhydrous solids or pastes, oil-in-water emulsions, suspensions, microemulsions, microcapsules, microgranules, ionic (liposomes) or non-ionic vesicular dispersions, creams, skin lotions, powders, ointments, sprays and concealing sticks. In addition, foam formulations and aerosol formulations containing compressed propellants are contemplated as possible formulations.

In addition, the cosmetic product of the present invention may further comprise adjuvants such as any other components that are conventionally used in the cosmetic field. Examples of such adjuvants include fats, organic solvents, solubilizer, thickeners, gelling agents, softeners, antioxidants, suspending agents, stabilizers, foaming agents, aromatics, surfactants, water, ionic or non-ionic emulsifiers, fillers, and chelators, preservatives, vitamins, screening agents, humectants, essential oils, dyes, pigments, hydrophilic or lipophilic activating agents and lipid vesicles. These adjuvants may be introduced in amounts that are conventionally used in the dermatological field.

The functional cosmetic product of the present invention particularly has an excellent anti-inflammatory effect, and thus can be effectively used as a functional cosmetic product that alleviates the symptom of inflammation caused by atopic dermatitis, which is an inflammatory disease of the skin to which cosmetic products are applied, or a burn.

As evident from the results of analysis of biological mechanisms as described below, Ramalin contained as an active ingredient in the functional cosmetic product of the present invention has excellent anti-inflammatory activity.

Thus, it will be obvious to those skilled in the art that Ramalin will exhibit excellent effects when it is used in cosmetic products.

EXAMPLES

Hereinafter, the present invention will be described in further detail with reference to examples. It will be obvious to a person having ordinary skill in the art that these examples are illustrative purposes only and are not to be construed to limit the scope of the present invention. That is, the following steps will be described as one illustrative ones and do not limit the scope of the present invention.

Example 1

Isolation of Ramalin 672 g of a freeze-dried and ground *Ramalina terebrata* sample was extracted three times with a mixture of methanol and water (5 L, 80:20 v/v) and freeze-dried, thereby obtaining 83 g of a crude extract. The crude extract was dissolved in 1 L of distilled water, and then extracted with 1 L of n-hexane and chloroform ($CHCl_3$) to obtain 12.7 g of a n-hexane extract, 9.1 g of a chloroform extract ($CHCl_3$) and 61.0 g of a water-soluble extract. The water-soluble extract showed highly activity ($IC_{50}$=9 μg/ml) against DPPH free radicals. A portion (5 g) of the water-soluble extract was then subjected to automated mild pressure liquid chromatography (MPLC) using a stepwise gradient solvent system of 0%, 20%, 40%, 60%, 80% and 100% methanol in water. The fraction dissolved in 0% methanol-water mixture showed high activity ($IC_{50}$=8 μg/ml) against DPPH free radicals, and a portion (100 mg) of this extract was subjected to semi-preparative reverse phase HPLC using a $C_{18}ODS$ column (250 cm×10 cm). The used gradient solvent system was 0% methanol in water (containing 0.1% formic acid) over 10 min, 20% methanol over 20 min, and 100% methanol over 30 min. The flow rate was 2 ml/min.

Compounds were detected by UV absorption at 280 nm. The fifth fraction (45 mg; $t_R$=18.88 min) was found to exhibit the highest activity ($IC_{50}$=1 μg/ml) against DPPH free radicals and was therefore subjected to further purification by using repeated semi-preparative HPLC using a $C_{18}ODS$ column (250 cm×10 cm). The gradient solvent system was 10-30% acetonitrile in water (0.1% formic acid) over 50 min with a flow rate of 2 ml/min. As a result, 30 mg of Ramalin was obtained at 8.26 min and showed an activity of $IC_{50}$=0.99 μg/mL against DPPH free radicals.

ESIMS (electrospray ionization mass spectrometry) data were obtained using a Mariner ESI-MS instrument (Perseptive Biosystem, USA). NMR spectra (1D and 2D) were recorded in acetone-$d_6$ in addition to $D_2O$ using a JEOL JNM ECP-400 spectrometer (400 MHz for $^1H$ and 100 MHz for $^{13}C$), and chemical shifts were referenced relative to the remaining acetone-$d_6$ ($d_H/d_C$=2.22/21.0). HMQC and HMBC experiments were optimized for $^1J_{CH}$=140 Hz and $^nJ_{CH}$=8 Hz. As a result, compound was found to have a structure of the following formula 1.

[Formula 1]

Unless specified otherwise, all compounds used in the following examples were purchased from Sigma Chemical Co. (US). Also, all cell cultures, thioglycollate cultures and Ramalin were assayed for any endotoxin contamination using the Limulus lysate test (E-Toxate kit, Sigma, US) and the level of endotoxin was found to be 10 pg/ml or less.

Example 2

Effect of Ramalin Treatment on the Production of Nitric Oxide in Macrophages Treated with LPS In order to examine the effect of pre-treatment with Ramalin on the LPS-induced production of NO, verification was performed using the mouse macrophage line RAQ 264.7 (ATCC, Rockville, Md., US). The cells were cultured in RPMI 1640 medium (GIBCO, Grand Island, N.Y., US) supplemented with 2 mM L-glutamine, 100 IU/ml penicillin, 100 μl/ml streptomycin and 10% heat-inactivated fetal bovine serum (FBS: Carlsband, US). The cell culture was performed under the conditions of 37° C., 5% $CO_2$ and wet air, and the medium was replaced twice a week.

The macrophages were cultured in a 96-well tissue culture dish at a concentration of $1\times10^5$ cells/well, and treated with Ramalin for 2 hours in order to examine cytotoxicity. The cell viability was analyzed by the 3-(4,5-dimethylthiazol-2-yl)-2,5-diphenyltetrazolium bromide (MTT) assay which measures the mitochondrial activity of viable cells. The reduction of MTT to formazan was quantified by measuring the optical density at 550 nm using a Molecular Device microplate reader (Sunnyvale, Calif., US).

As a result, treatment with 0.1, 1 and 10 μg/ml of Ramalin had no cytotoxicity, and thus showed no change in cell viability. However, cytotoxicity appeared at a Ramalin concentration of 100 μg/ml (data not shown).

In order to determine the accumulation of nitrogen dioxide ($NO_2^-$), a test group pretreated with Ramalin and an untreated control group were prepared. Medium was pretreated with 0.1, 1 and 10 μg/ml of Ramalin 2 hours before treatment with 1 μg/ml of LPS. The amount of nitrogen dioxide accumulated in the medium was determined by transferring 100 μl of the supernatant from each well into an empty well dish, adding 100 μl of Griess solution (a 1:1 mixture of 0.1% naphthylethylene diamine dihydrochloride in distilled water and 1% sulfanilamide in 5% $H_3PO_4$) thereto, and then measuring the absorbance at 550 nm using a Molecular Device microplate reader (Sunnyvale, Calif., US). The concentration of nitrogen dioxide can be calculated from a standard curve for nitrite ($NaNO_2$). The level of nitrogen dioxide may be indicative of the amount of nitric oxide (NO).

Figure 1:
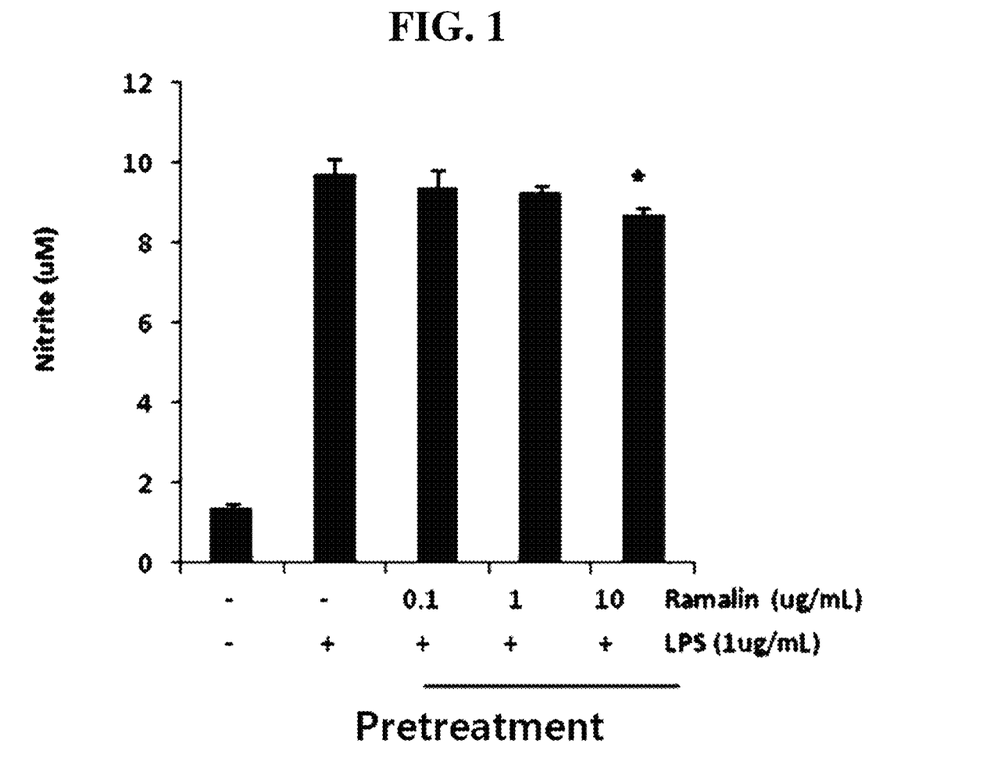
FIG. 1 shows the results of measuring the level of nitrite in media for 24 hours after LPS treatment.

As a result, as can be seen in FIG. 1 showing the concentration of nitrite, pre-treatment with 10 μg/ml of Ramalin resulted in a significant decrease in the production of nitric oxide. Also, even at Ramalin concentrations lower than 10 μg/ml, a decrease in the production of nitric oxide appeared.

Statistical analysis was performed by measuring the mean±S.E.M. statistical difference between the groups using by one-way ANOVA with Fisher's PLSD. Unless specified otherwise, the same statistical analysis method was used in the following examples.

Example 3

Effect of Ramalin Treatment on the Production of iNOS in Macrophages Treated with LPS In order to examine the effect of pretreatment with Ramalin on the LPS-induced production of iNOS, the production of mRNA was analyzed by RT-PCR, and the production of protein was analyzed by Western blot. This is because a decrease in the production of NO is attributable to the inhibition of production of iNOS. For RT-PCR, cells were treated with LPS and Ramalin as described in Example 2, and then the total RNA of the cultured cells was collected using Trizol (Invitrogen, US). Then, the total RNA was amplified by Superscript one step RT-PCR using a PLATINUM Taq kit (Invitrogen, US). The PCR product was loaded onto 1.2% agarose gel which was then stained with EtBr. As a control, GAPDH was used. The PCR amplification was performed using the following primer sequences: for iNOS-F, 5'-AGA CTG GAT TTG GCT GGT CCC TCC-3' (SEQ ID NO: 1); for iNOS-R, 5'-AGA ACT GAG GGT ACA TGC TGG AGC-3' (SEQ ID NO: 2); for GAPDH-F, 5'-CCA TGG AGA AGG CTG GGG-3' (SEQ ID NO: 3); for GAPDH-R, 5'-CAA AGT TGT CAT GGA TGA CC-3' (SEQ ID NO: 4).

Figure 2:
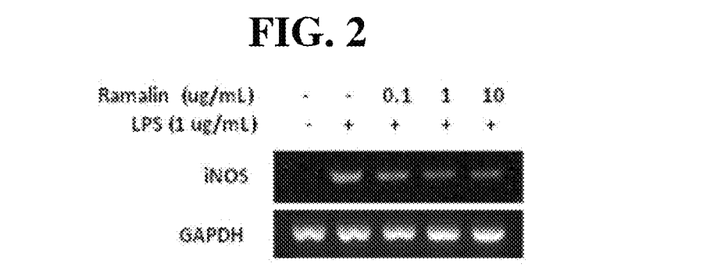
FIG. 2 shows the results of RT-PCR analysis conducted to examine the expression levels of iNOS mRNA and GAPDH mRNA as a control.

As a result, as can be seen in FIG. 2, the expression of iNOS mRNA in the groups treated with various concentrations of Ramalin was lower than that in the group treated with the control. However, the inhibition of the expression of iNOS mRNA was concentration-dependent, and this inhibitory effect was significant compared to that of the control GADPH.

For Western blot analysis, cells were treated with LPS and Ramalin as described in Example 2, washed twice with PBS (phosphate buffered saline), and then lysed in lysis buffer (50 mM Tris, pH 8.0, 150 mM NaCl, 0.1% sodium dodecyl sulfate, 0.5% sodium deoxycholate, 1% NP40, 100 μg/ml phenylsulfonyl fluoride, 2 μg/ml aprotinin, 1 μg/ml pepstatin, and 10 μg/ml leupeptin). Then, the cell lysate was kept on ice for 30 minutes and centrifuged at 15000 g at 40° C. for 20 minutes, and the supernatant was collected. The density of protein was analyzed using a Bio-Rad protein assay (Bio-Rad Lab, Hercules, Calif.) and BSA (Sigma). The total lysate (20 μg) was resolved on 7.5% SDS-polyacrylamide gel, and it was transferred to an immobilon polyvinylidene difluoride membrane (Amersham, Arlington Heights, Ill.) and labeled with an antibody. The blot was analyzed using an enhanced chemoluminescence (ECL) kit (Amersham). All the antibody blot experiments were performed using anti-beta actin antibody as a protein loading control.

Figure 3:
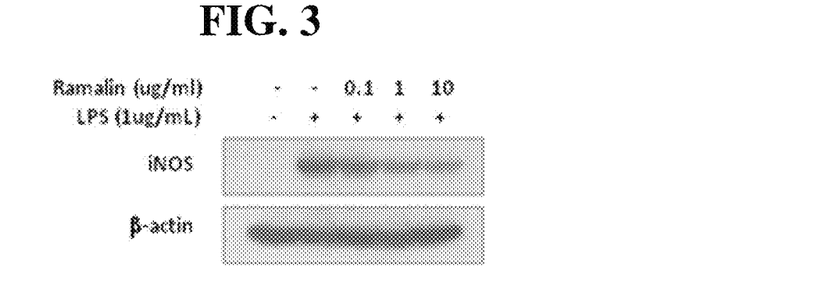
FIG. 3 shows the results of Western blot analysis conducted to examine the level of iNOS protein and the level of β-actin as a control.

As a result, as can be seen in FIG. 3, the expression of iNOS protein in the groups treated with various concentrations of Ramalin was lower than that in the group treated with the control. However, the inhibition of the expression of iNOS protein was concentration-dependent, and this inhibitory effect was significant compared to that of the control GADPH.

Example 4

Effect of Ramalin Pretreatment on TLR4 Macrophages Treated with LPS

TLR4 (toll-like receptor 4) signaling is known to play a pivotal role in the induction of inflammatory responses, and LPS is a ligand that is recognized by TLR4. Thus, in order to analyze the effect of Ramalin pretreatment on the expression of TLR4, the level of surface expression of TLR4, the mRNA level of TLR4 and the level of TLR4 protein were measured. The analysis of TLR4 was performed in the following manner.

Macrophage Raw264.7 cells were subcultured, and then seeded in a 96-well plate at a density of $1\text{-}4\times10^4$ cells/well and cultured. After 12 hours of culture, the cells were treated with 0.1, 1 and 10 μg/mL of Ramalin and incubated for 2 hours. The supernatant was removed from the cultured cells, which were then washed with d-PBS and treated with LPS (1 μg/mL). After 8 hours, the expression level of TLR4 on the cell surface was measured by an ELISA assay. After the supernatant has been removed, the cells were washed twice with d-PBS and incubated in 200 mL of blocking buffer (1% FBS in d-PBS) at room temperature for 30 minutes to induce non-specific binding. The cells were washed three times with washing buffer) (0.05% Tween 20 in d-PBS), and 100 μL of a 1:500 dilution of primary antibody TLR4 in blocking buffer was added thereto and allowed to stand for 2 hours at room temperature. Then, the cells were washed five times with washing buffer, and 100 μL of a 1:1000 dilution of alkaline phosphatase-conjugated anti-rat secondary antibody in blocking buffer was added thereto and allowed to stand at room temperature for 1 hour, after which the cells were washed seven times with washing buffer. 100 μL of a peroxidase substrate was added thereto and incubated at room temperature for 30 minutes in the absence of light. The absorbance at 650 nm was measured using a microplate reader.

The level of TLR4 mRNA and the level of TLR4 protein were measured as described in Example 3.

Figure 4:
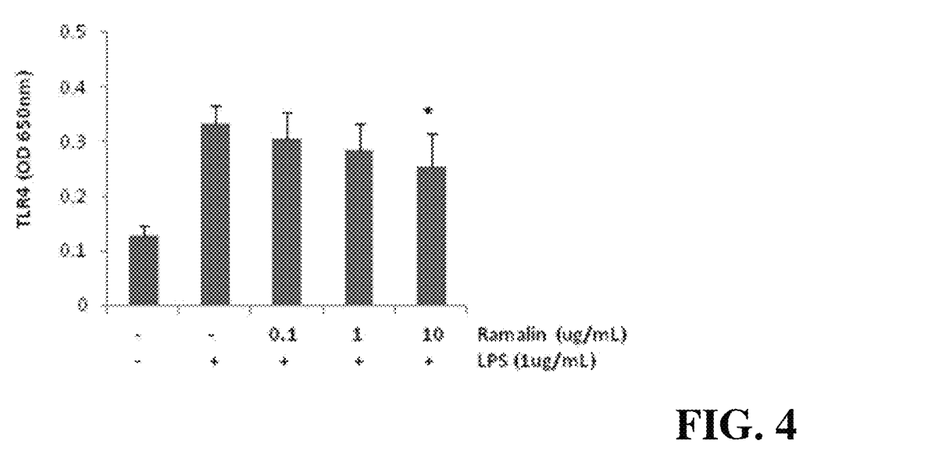
FIG. 4 shows the results of measuring the surface expression level of TLR4 for 24 hours after LPS treatment.
Figure 5:
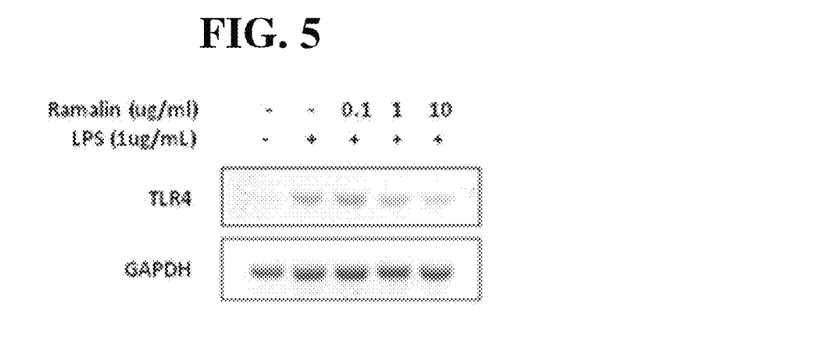
FIG. 5 shows the results of RT-PCR analysis conducted to the expression levels of TLR4 mRNA and GAPDH mRNA as a control.
Figure 6:
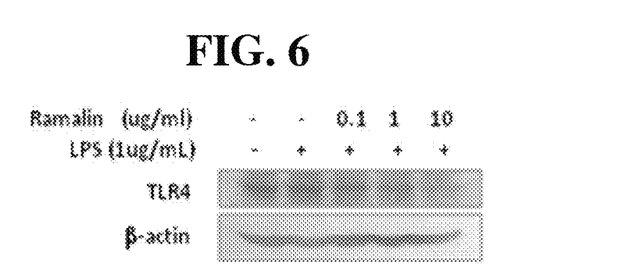
FIG. 6 shows the results of Western blot analysis conducted to examine the level of TLR4 protein and the level of β-actin as a control.

As a result, as can be seen in FIG. 4, the LPS-induced surface expression of TLR4 in the test groups treated with Ramalin significantly decreased. In addition, the levels of both TLR4 mRNA and protein decreased (see FIGS. 5 and 6).

Example 5

Effect of Ramalin Pretreatment on NF-κB in Macrophages Treated with LPS

NF-κB is a transcriptional factor that is most important in the expression of iNOS. Thus, in order to examine the effect of Ramalin pretreatment on NF-κB, the expression level of luciferase was analyzed. One method for analyzing the expression of NF-κB is a luciferase assay. The luciferase assay is a test method for determining the activation of a promoter. In the luciferase assay, the promoter region of a specific gene is ligated into a vector containing luciferase, and when the promoter is activated, light is emitted.

Specifically, in order to introduce the promoter region of NF-κB, a suspension of cells ($1\times10^6$ cells/mL) in a medium containing 10% FBS, penicillin (100 IU/mL) and streptomycin (100 mg/mL) was incubated in a 60 mm Petri dish, and the cells were stabilized for 24 hours. Then, the cells were treated with a transfection mixture containing the promoter region to be introduced and were incubated for 24 hours. Then, the cells were incubated under varying conditions. The supernatant was removed from the incubated cells which were then washed with d-PBS. 200 μl/well of 1× lysis buffer (25 mM Tris-phosphate, pH 7.8, 2 mM DTT, 2 mM 1,2-diaminocyclohexane-N,N,N,N' tetracetic acid, 10% glycerol, 1% triton X-100, 1.25 mg/mL lysozyme, 2.5 mg/mL BSA) was added to the cells which were lysed by stirring at room temperature. The luciferase activity of the cell lysate was measured using a Bright-Glo luciferase assay system according to the manufacturer's instruction.

Meanwhile, the p65 subunit of NF-κB is known to play an important role in the initiation of transcription of inflammatory genes. Thus, the expression level of p65 subunit protein was analyzed by Western blot in order to examine the effect of Ramalin. In addition, it is known that IκBα is an NF-κB inhibitor that usually binds to NF-κB to inhibit the activity of NF-κB, and LPS or IFN-gamma promotes the separation of IκBα so that NF-κB is activated. Thus, the level of IκBα protein was analyzed for 60 minutes.

The activity of luciferase was measured by transfection and reporter gene assays. Specifically, RAW 264.7 cells (5×10⁵ cells/ml) were plated in a 6-well dish and transfected with pGL3-NF-κB and a pCMV-beta-gal plasmid using LipofectAMINE Plus (Sigma). For transfection, a mixture of 0.5 µg pGL3-NF-κB and 0.2 µg pCMV-beta-gal in LipofectAMINE Plus solution was added to the cells, and after 4 hours, the cells were pretreated with Ramalin for 4 hours, and after 2 hours, the cells were treated with LPS. Then, the cells were lysed in 200 µl of lysis buffer (24 mM Tris-HCl (7.8 PH), 2 mM dithiotreitol, 2 mM EDTA, 10% glycerol and 1% Triton X-100), and then the luciferase activity of 10 µl of the cell lysate was analyzed. The test for each of luciferase and beta-galactosidase was performed three times by three different persons, and then luciferase activity was normalized with beta-galactosidase activity.

Figure 7:
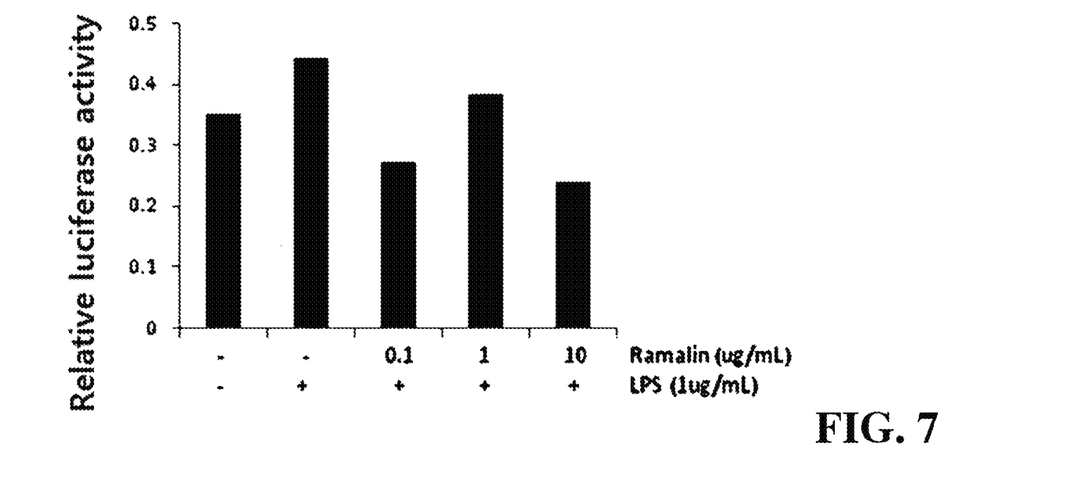
FIG. 7 shows the results obtained by transforming RAW 264.7 cells with a pGL3-NF-κB-Luc reporter plasmid and pCMV-β-gal, treating the cells with LPS for 4 hours and then measuring relative luciferase activities.

As a result, as can be seen in FIG. 7, luciferase activity increased by 1.5 times due to LPS treatment, but when Ramalin treatment was performed, there was no increase in luciferase activity.

Figure 8:
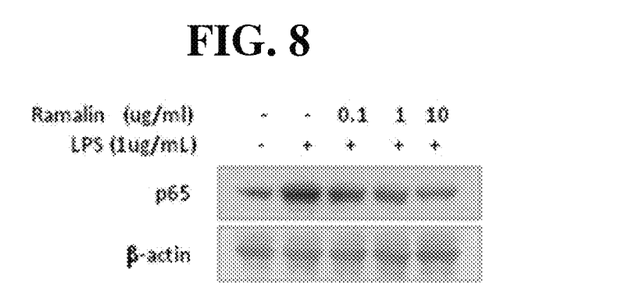
FIG. 8 shows the results of Western blot analysis conducted to measure the amount of p65 nuclear protein in order to analyze the translocation of NF-κB.
Figure 9:
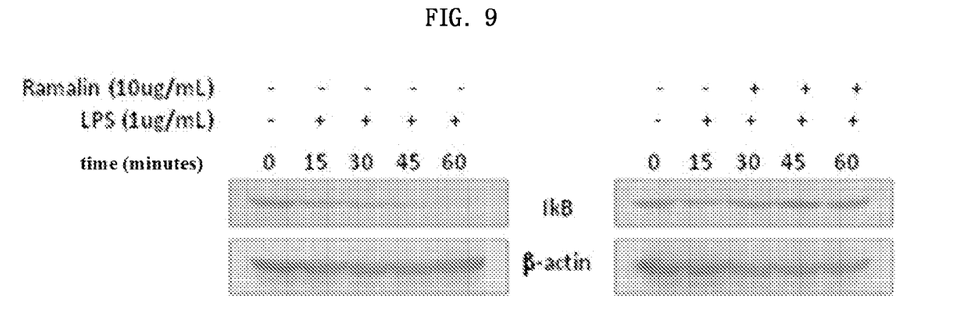
FIG. 9 shows the results obtained by pre-treating or not pre-treating cells with 10 μg/ml of Ramalin, treating the cells with 1 μg/ml of LPS for the indicated time, and then analyzing the cells by Western blot analysis with anti-IκBα antibody.

The levels of p65 and IκBα proteins were measured by Western blot analysis as described in Example 3. As a result, as can be seen in FIG. 8, the production of p65 NF-κB in the macrophages pretreated with Ramalin was significantly lower than that in the macrophages not pretreated with Ramalin. In addition, as can be seen in FIG. 9, in the case in which the macrophages were pretreated with Ramalin, IκBα was maintained in a state bound to NF-κB so that the amount thereof was shown to be smaller than that in the case in which the macrophages were not pretreated with Ramalin. The above results suggest that Ramalin inhibits the intermediate stage of the inflammatory response induced by LPS or IFN-gamma, thereby inhibiting the activation of NF-κB.

Example 6

Effect of Ramalin Pretreatment on p38 MAPK, ERK1/2 and JNK in Macrophages Treated with LPS p38 MAPK, ERK1/2 and JNK kinase pathways are known as signaling stages that regulate the intermediate stage of inflammatory responses. Thus, the expression levels of p38 MAPK, ERK1/2 and JNK were analyzed in order to examine the effect of Ramalin pretreatment. This Example was performed in the same manner as Example 3, and the analysis of the levels of the proteins was performed by Western blot analysis in the same manner as Example 3.

Figure 10:
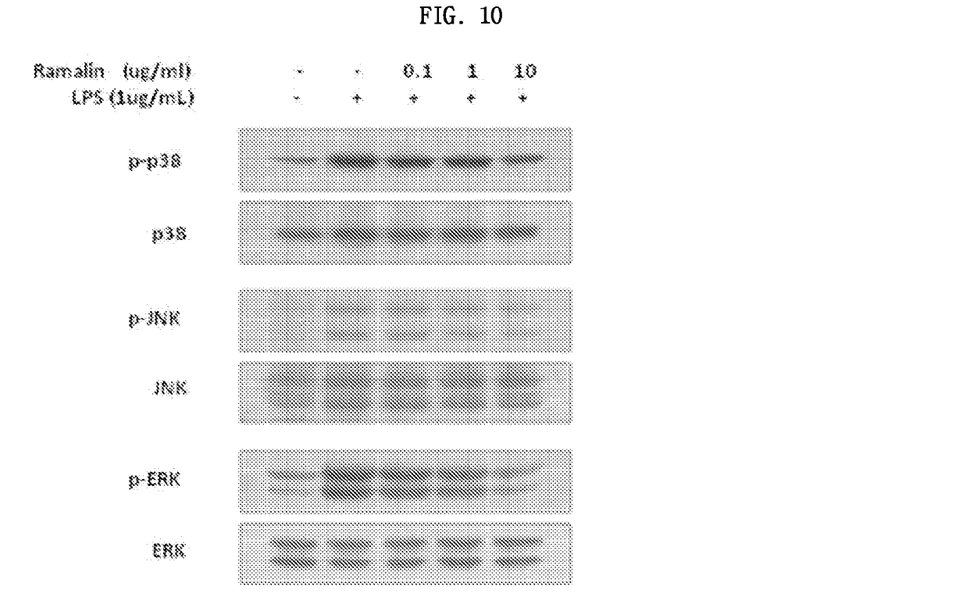
FIG. 10 shows the effect of Ramalin on the activation of p-p38, p-JNK and p-ERK in LPS-stimulated macrophages and shows the results obtained by pre-treating cells with Ramalin for 1 hour, treating the cells with LPS for 20 minutes and then analyzing the total cell lysate by Western blot analysis.

As a result, as can be seen in FIG. 10, the levels of p38, ERK and JNK proteins did not change regardless of Ramalin pretreatment, but the levels of p-p38, p-ERK and p-JNK, which are phosphorylated forms, decreased in a manner dependent on the concentration of Ramalin used to pre-treat the cells. This suggests that Ramalin inhibits the phosphorylation of each of the proteins, thereby inhibiting inflammatory responses.

Example 7

Effect of Ramalin Pretreatment on the Volume of Edema in Rats Treated with LPS

In Examples 2 to 6 above, the effects of Ramalin pretreatment were analyzed in vitro. In Example 7, a test was performed using living rats in order to examine Ramalin actually has an anti-inflammatory effect. Thus, rats were administered with each of a vehicle (control), 50 mg/kg of Ramalin, 100 mg/kg of Ramalin and indomethacin (anti-inflammatory agent, positive control), and then inflammatory responses in the rats were induced using carrageenan that is a kind of IDS, and the anti-inflammatory effect of Ramalin was evaluated based on the rate of increase in the volume of foot edema.

A pharmaceutical composition for preventing or treating inflammatory disease or immune disease, which contains, as an active ingredient, Ramalin having a structure of the following formula 1 or a pharmaceutically acceptable salt thereof:

[Formula 1]

Carrageenan used in the test was purchased from Sigma (c-1867, CAS No.: 9000-07-1, EC No.: 232-524-2), and particularly a mixture of kappa-carrageenan and lambda-carrageenan was used. Carrageenan is used as a food additive for increasing the stickiness, viscosity and emulsion stability of foods. In addition, it is used as a thickener, a gelling agent, a stabilizer or the like. Carrageenan is obtained by extracting seaweeds, including *Chondrus* sp., *Eucheuma* sp., *Gigartina* sp., *Hypnea* sp. and *Iridaea* sp., which are red algae known as Irish mosses, with water or hot alkaline aqueous solution, and purifying the extract, and the main components thereof are ι(iota)-carrageenan, κ(kappa)-carrageenan, and λ(lambda)-carrageenan. Particularly, lambda-carrageenan (about 1-2%) is used as an edema-inducing material in inflammation-related animal tests.

The rats used in the test were male Sprague-Dawley rats (150-200 g, younger than 6 weeks) and purchased from Daehan Bio Co., Ltd. (Korea). The animals were maintained in the laboratory in accordance with internationally accepted principles for laboratory animal use and care. The carrageenan used was a mixture of kappa-carrageenan and lambda-carrageenan and purchased from Sigma (USA), and the indomethacin used was also purchased from Sigma (USA).

Figure 11:
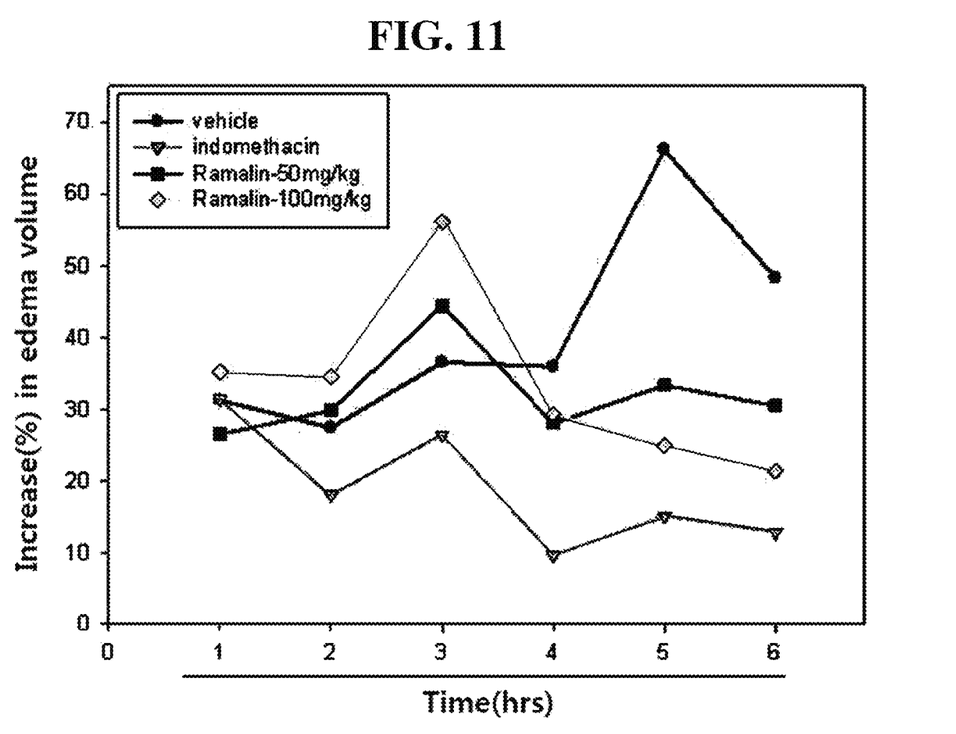
FIG. 11 shows the results of measuring the volume of rat foot edema induced by carrageenan and indicates that a group administered with Ramalin (100 mg/kg) showed an anti-inflammatory effect of about 50% after 6 hours compared to a control group administered with a vehicle and a positive control group administered with indomethacin (Sigma1-7378).

Ramalin was used as a solution in 500 µl of saline at concentrations of 50 mg/kg and 100 mg/kg, the vehicle used was saline, and indomethacin was used as a solution in 500 µl of saline at a concentration of 10 mg/kg. Each of Ramalin, the vehicle and indomethacin was administered to each rat, and after 1 hour, 100 µl of 1% carrageenan in saline was injected subcutaneously into the hind feet of the rats. Then, the thickness of the foot of each rat was measured for 6 hours, and the rate of increase in the volume of edema was determined. The results of the measurement are shown in FIG. 11. At each point of time, three measurements were obtained and averaged.

As can be seen in FIG. 11, the rat administered with 100 mg/kg of Ramalin showed a high anti-inflammatory effect and a significant difference in edema volume from the control group administered with the vehicle. This suggests that pretreatment with Ramalin significantly inhibit inflammatory responses.

INDUSTRIAL APPLICABILITY

The present invention provides a pharmaceutical composition containing Ramalin as an active ingredient. The pharmaceutical composition shows an excellent effect of inhibiting the production of nitric oxide (NO) by inhibiting the production of iNOS, compared to conventional pharmaceutical compositions. Thus, the pharmaceutical composition of the invention has the effect of treating inflammatory disease or immune disease by inhibiting excessive inflammatory responses and immune responses and can be used in functional foods and functional cosmetic products.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

[Formula 1]

The invention claimed is:

1. A method of reducing inflammation in a subject comprising administering a composition comprising Ramalin or a pharmaceutically acceptable salt thereof as an active ingredient to a subject, wherein the Ramalin has a structure of the following formula 1:

2. The method of claim 1, wherein the composition further contains a suitable carrier, excipient or diluent which is commonly used in preparation of pharmaceutical compositions.

3. The method of claim 1, wherein the administering comprises providing a functional food to the subject, wherein the functional food contains, as an active ingredient, Ramalin.

4. The method of claim 1, wherein the administering comprises providing to the subject a functional cosmetic product comprising Ramalin.

5. The method of claim 1, wherein the composition comprises 0.1 µg/ml to 10 µg/ml of Ramalin or a pharmaceutically acceptable salt thereof.

6. The method of claim 3, wherein the functional food comprises 0.1 µg/ml to 10 µg/ml of Ramalin.

7. The method of claim 4, wherein the functional cosmetic product comprises 0.1 µg/ml to 10 µg/ml of Ramalin.

8. The method of claim 1, wherein the composition is formulated in combination with an anti-inflammatory agent.

9. A method of inhibiting production of nitric oxide in cells of a subject comprising administering a composition comprising an isolated form of Ramalin or a pharmaceutically acceptable salt thereof as an active ingredient to the subject, wherein the Ramalin has a structure of the following formula 1:

[Formula 1]

10. The method of claim 9, wherein the composition further contains a suitable pharmaceutically acceptable carrier, excipient or diluent.

11. The method of claim 9, wherein the composition is formulated in combination with an anti-inflammatory agent.

12. The method of claim 9, wherein the composition comprises 0.1 µg/ml to 40 µg/ml of Ramalin or a pharmaceutically acceptable salt thereof.

13. The method of claim 1, wherein the Ramalin or a pharmaceutically acceptable salt thereof is administered in an amount of 0.1 µg/ml to 40 µg/ml.

14. The method of claim 3, wherein the functional food contains Ramalin in an amount of 0.1 µg/ml to 40 µg/ml.

15. The method of claim 4, wherein the functional cosmetic product contains Ramalin in an amount of 0.1 µg/ml to 40 µg/ml.

* * * * *

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial
<220> FEATURE:
<223> OTHER INFORMATION: promoter

<400> SEQUENCE: 1
agactggatt tggctggtcc ctcc                                          24

<210> SEQ ID NO 2
<211> LENGTH: 24
<212> TYPE: DNA
<213> ORGANISM: Artificial
<220> FEATURE:
<223> OTHER INFORMATION: promoter

<400> SEQUENCE: 2
agaactgagg gtacatgctg gagc                                          24

<210> SEQ ID NO 3
<211> LENGTH: 18
<212> TYPE: DNA
<213> ORGANISM: Artificial
<220> FEATURE:
<223> OTHER INFORMATION: promoter

<400> SEQUENCE: 3
ccatggagaa ggctgggg                                                 18

<210> SEQ ID NO 4
<211> LENGTH: 20
<212> TYPE: DNA
<213> ORGANISM: Artificial
<220> FEATURE:
<223> OTHER INFORMATION: promoter

<400> SEQUENCE: 4
caaagttgtc atggatgacc                                               20
```

UNITED STATES PATENT AND TRADEMARK OFFICE
CERTIFICATE OF CORRECTION

| | | |
|---|---|---|
| PATENT NO. | : 9,539,227 B2 | Page 1 of 1 |
| APPLICATION NO. | : 14/261551 | |
| DATED | : January 10, 2017 | |
| INVENTOR(S) | : Joung Han Yim et al. | |

It is certified that error appears in the above-identified patent and that said Letters Patent is hereby corrected as shown below:

In the Specification

Column 4, Lines 66-67: "which is corn only used" should be --which is commonly used--.

Signed and Sealed this
Twenty-eighth Day of February, 2017

Michelle K. Lee
*Director of the United States Patent and Trademark Office*